US00PP24887P2

(12) United States Plant Patent
Green, Jr.

(10) Patent No.: US PP24,887 P2
(45) Date of Patent: Sep. 16, 2014

(54) *CAMELLIA* PLANT NAMED 'GREEN 99-016'

(50) Latin Name: *Camellia sasanqua*
Varietal Denomination: Green 99-016

(71) Applicant: Robert M. Green, Jr., Fairhope, AL (US)

(72) Inventor: Robert M. Green, Jr., Fairhope, AL (US)

(73) Assignee: Plants Nouvean, LLC, Charleston, SC (US)

( * ) Notice: Subject to any disclaimer, the term of this patent is extended or adjusted under 35 U.S.C. 154(b) by 81 days.

(21) Appl. No.: 13/815,068

(22) Filed: Jan. 29, 2013

(51) Int. Cl.
*A01H 5/00* (2006.01)

(52) U.S. Cl.
USPC ..... Plt./243

(58) Field of Classification Search
USPC ..... Plt./243
See application file for complete search history.

*Primary Examiner* — Anne Grunberg
(74) *Attorney, Agent, or Firm* — Penny J. Aguirre

(57) ABSTRACT

A new cultivar of *Camellia sasanqua* named 'Green 99-016', characterized by its dense and upright plant habit, its white double flowers (peony-form) that have a very high number of petals and petaloids imparting a carnation-like appearance, its vigorous growth habit, its dark green foliage, and its good resistance to *Phytophora* sp. and *Glomerella*.

2 Drawing Sheets

Botanical classification: *Camellia sasanqua*.
Variety denomination: 'Green 99-016'.

CROSS REFERENCE TO A RELATED APPLICATION

This application is co-pending with a U.S. Plant Patent Application filed for a plant derived from the same breeding program that is entitled *Camellia* Plant Named 'Green 99-031' (U.S. Plant patent application Ser. No. 13/815,071).

BACKGROUND OF THE INVENTION

The present invention relates to a new and distinct cultivar of *Camellia sasanqua*. The new cultivar will be referred to hereafter by its cultivar name, 'Green 99-016'. 'Green 99-016' is grown for use as a landscape shrub.

The new *Camellia* arose from on ongoing breeding program conducted by the Inventor in Fairhope, Ala. that began in 1992. The objective of the breeding program is to produce new cultivars of *Camellia* with compact plant habits, vigorous growth habits, improved disease resistance and extended bloom periods. 'Green 99-016' originated from seed derived from open pollination of the cultivar 'Mine-No-Yuki' (not patented) in 1999. The male parent is therefore unknown. The new *Camellia* was selected as a single unique plant amongst the resulting seedlings in fall of 2002.

The new cultivar was first asexually propagated by stem cutting by the Inventor in summer of 2003 in Fairhope, Ala. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia* as observed in Fairhope, Ala. These attributes in combination distinguish 'Green 99-016' as a unique cultivar of *Camellia*.

1. 'Green 99-016' exhibits a dense, upright plant habit.
2. 'Green 99-016' exhibits white double flowers (peony-form) that have a very high number of petals and petaloids imparting a carnation-like appearance.
3. 'Green 99-016' exhibits a vigorous growth habit.
4. 'Green 99-016' exhibits dark green foliage.
5. 'Green 99-016' has shown good resistance to *Phytophora* sp. and *Glomerella*.

The new cultivar of *Camellia* can be readily distinguished from its parent plant and other cultivars. 'Mine-No-Yuki', the female parent plant, differs from 'Green 99-016' in having a less dense and less upright plant habit, flowers with less petals and petaloids, lighter green foliage and in having a less vigorous growth habit as a young plant. 'Green 99-016' can also be compared to the cultivars 'Setsugekka' (not patented), 'Snow Flurry' (not patented) and 'Green 99-031'.'Setsugekka' and 'Snow Flurry' are similar to 'Green 99-016' in having double white flowers. 'Setsugekka' differs from 'Green 99-016' in having flowers with less petals and petaloids and that have some pink coloration when fully open, a less dense plant habit, and less vigor and disease resistance. 'Snow Flurry' differs from 'Green 99-016' in being a hybrid of *C. sasanqua* and *C. oleifera*, in having a less dense, less uniform and less upright plant habit, and in having leaves that are much lighter green in color. 'Green 99-031' is similar to 'Green 99-016' in having good disease restance, a dense plant habit, good vigor and dark green foliage. 'Green 99-031' differs from 'Green 99-016' in having slightly larger flowers that are pink in color, less double, and formal double in form.

BRIEF DESCRIPTION OF THE DRAWING

The accompanying colored photographs illustrate the overall appearance and distinct characteristics of the new *Camellia*, 'Green 99-016', as grown in Fairhope, Ala. The photographs were taken of four year-old plants of 'Green 99-016' as grown in a trial garden in in Fairhope, Ala.

The photograph in FIG. 1 provides view of the plant habit of 'Green 99-016'.

Figure 1:
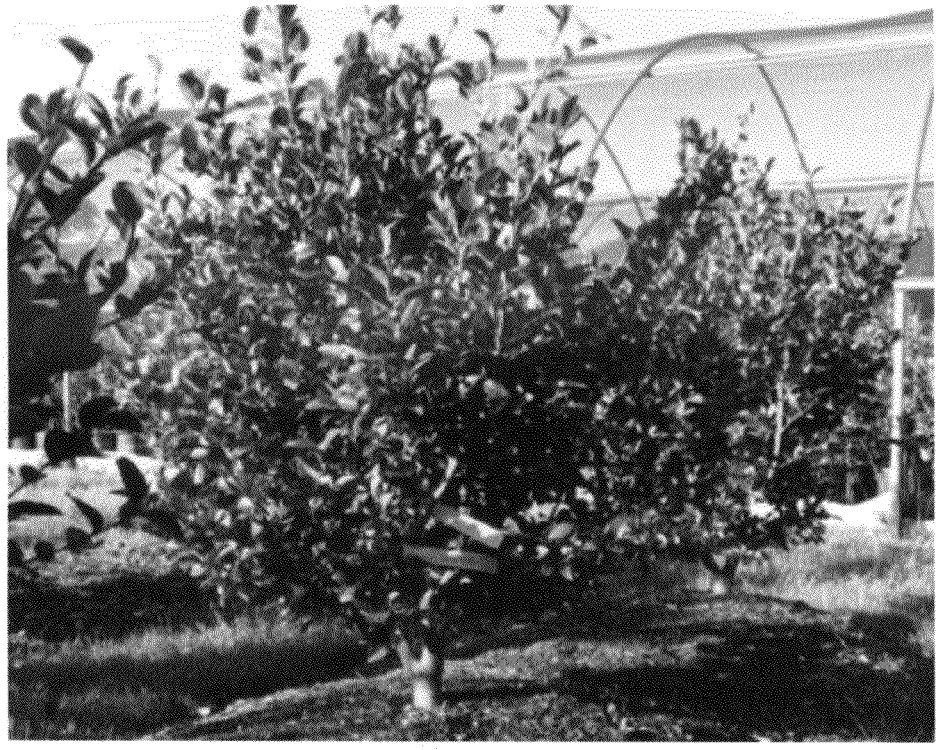
Figure 2:
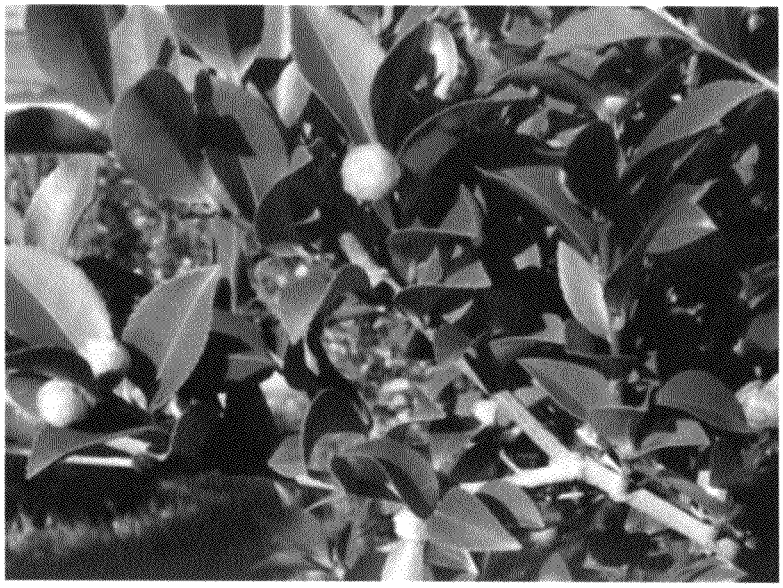

The photograph in FIG. 2 provides a view of the flower buds of 'Green 99-016'.

Figure 3:
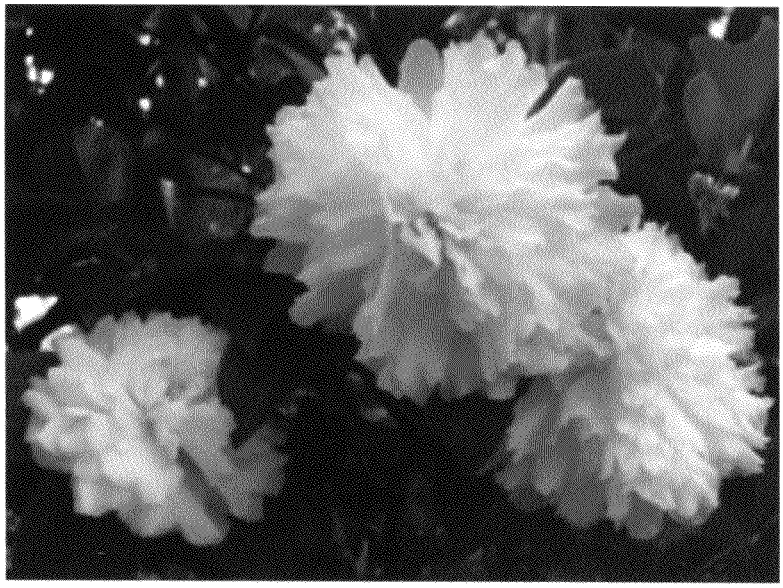

The photograph in FIG. 3 provides a close-up view of the flowers of 'Green 99-016'.

The colors in the photographs are as close as possible with digital photography techniques available, the color values cited in the detailed botanical description accurately describe the colors of the new *Camellia*.

DETAILED BOTANICAL DESCRIPTION

The following is a detailed description of the new cultivar as observed on 42 month-old plants of 'Green 99-016' as grown outdoors under 30% shade cloth in 3-gallon containers in Fairhope, Ala. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Seven to eight weeks in mid to late fall in Fairhope, Ala.

*Plant type.*—Evergreen shrub.

*Plant habit.*—Dense and upright.

*Height and spread.*—Up to 2.4 m (8 feet) in height and 1.5 m (5 feet) in width.

*Cold hardiness.*—At least in U.S.D.A. Zones 7a to 9.

*Diseases and pests.*—Has shown good resistance to *Phytophora* sp. and *Glomerella.*

*Propagation*.—Stem cuttings.

*Growth rate.*—Vigorous, even as a young plant.

Branch description:

*Stem shape.*—Round.

*Stem strength.*—Strong.

*Stem color.*—Young; 144B at the base then becoming 165A at the top, mature bark; 200B flushed with 165B at the base then becoming 165A towards the middle and top.

*Stem size.*—Lateral branches; 35 to 41 cm in length and 4 mm in width.

*Stem surface*.—Young; slightly glossy and densely covered with pubescent hairs 0.5 mm in length and 165A in color, smooth, slightly glossy, adult wood; bark-like, slightly rough to touch.

*Branching.*—Densely branched with an average of 18 lateral branches.

*Internode length.*—5 to 10 cm.

Foliage description:

*Leaf shape.*—Ovate to elliptic.

*Leaf division.*—Simple.

*Leaf base.*—Cuneate.

*Leaf apex.*—Acuminate.

*Leaf fragrance.*—None.

*Leaf margins.*—Serrate.

*Leaf arrangement.*—Alternate.

*Leaf attachment.*—Petiolate.

*Leaf substance*.—Thick and leathery with a high tolerance to stress.

*Leaf surface.*—Smooth and glabrous on both surfaces, glossy on upper surface and satiny on lower surface.

*Leaf size.*—Average of 4.5 cm in length and 1.5 cm in width.

*Leaf quantity.*—Average of 9 per branch 15 cm in length.

*Leaf venation.*—Pinnate, upper surface center 145A in color, lower surface center 145A, surrounding veins N137A in color.

*Leaf color.*—Young leaves upper surface; N137A and slightly suffused with 165A, young leaves lower surface; 146B, mature leaves upper surface; N137A, mature leaves lower surface; 146A.

*Petioles.*—Flattened, 2 mm in width and 6 mm in length, color upper surface 144B, color lower surface 144A.

*Stipules.*—None.

Inflorescence description:

*Inflorescence type.*—Solitary.

*Flower number.*—5 to 7 per lateral stem.

*Flower fragrance.*—Slightly fragrant.

*Flower longevity.*—About one week, self cleaning.

*Flower type.*—Fully double, peony form.

*Flower aspect.*—Outward to slightly upright.

*Flower size.*—Average of 7 cm in diameter and 3.5 cm in depth.

*Peduncles*.—None, flowers are sessile to stem.

*Flower buds.*—Globose in shape, average of 1.5 cm in length and width, color 144C, apex NN155B.

*Sepals.*—5, round in shape and strongly cupped inward, imbricate, margin is entire, color of upper and lower surface; 144C, both surfaces are glabrous and shiny, average of 8 mm in length and width, apex is obtuse, base is truncate.

*Petals.*—28 to 30, cordate in shape, upper and lower surface is glabrous and dull, entire margin but slightly wavy with apex cordate, cuneate base, average of 3 cm in length and 2 cm width, fully open flowers upper and lower surface; NN155B, non-fading.

*Petaloids.*—38 to 46, cordate to irregular in shape, upper and lower surface glabrous and dull, entire margin but slightly wavy with apex typcially cordate, average of 1.6 cm in length and 9 mm in width, color upper and lower surface when fully open; NN155B.

Reproductive organs:

*Pistil.*—None, petaloid and not distiguishable.

*Stamens.*—Petaloid or poorly developed, pollen has not been observed.

*Fruits and seed.*—Fruit has not been observed, presumed sterile.

It is claimed:

1. A new and distinct cultivar of *Camellia* plant named 'Green 99-016' as herein illustrated and described.

* * * * *